US011382865B2

(12) United States Patent
Kanikanti et al.

(10) Patent No.: US 11,382,865 B2
(45) Date of Patent: Jul. 12, 2022

(54) PHARMACEUTICAL PREPARATION AND METHOD FOR ITS MANUFACTURE

(71) Applicant: BAYER ANIMAL HEALTH GMBH, Leverkusen (DE)

(72) Inventors: Venkata-Rangarao Kanikanti, Leverkusen (DE); Patrick Billian, Brieselang (DE)

(73) Assignee: BAYER ANIMAL HEALTH GMBH, Leverkusen (DE)

( * ) Notice: Subject to any disclaimer, the term of this patent is extended or adjusted under 35 U.S.C. 154(b) by 0 days.

(21) Appl. No.: 16/467,922

(22) PCT Filed: Nov. 30, 2017

(86) PCT No.: PCT/EP2017/081049
§ 371 (c)(1),
(2) Date: Jun. 7, 2019

(87) PCT Pub. No.: WO2018/104150
PCT Pub. Date: Jun. 14, 2018

(65) Prior Publication Data
US 2020/0069591 A1 Mar. 5, 2020

(30) Foreign Application Priority Data
Dec. 9, 2016 (EP) .................................... 16203308

(51) Int. Cl.
| A61K 9/24 | (2006.01) |
| A61K 9/20 | (2006.01) |
| A61K 31/27 | (2006.01) |
| A61K 31/35 | (2006.01) |
| A61K 31/4985 | (2006.01) |
| A61K 31/506 | (2006.01) |

(52) U.S. Cl.
CPC ............ *A61K 9/209* (2013.01); *A61K 9/2095* (2013.01); *A61K 31/27* (2013.01); *A61K 31/35* (2013.01); *A61K 31/4985* (2013.01); *A61K 31/506* (2013.01)

(58) Field of Classification Search
CPC ...... A61K 9/209; A61K 9/2095; A61K 31/27; A61K 31/35; A61K 31/4985; A61K 31/506; A61P 43/00; A61P 33/10; A61P 33/12
See application file for complete search history.

(56) References Cited

U.S. PATENT DOCUMENTS

| 4,999,226 | A | 3/1991 | Schock et al. |
| 5,030,622 | A | 3/1991 | Herumuuto et al. |
| 5,650,169 | A | 7/1997 | Conte et al. |
| 6,489,303 | B2 | 12/2002 | Jancys |
| 7,348,027 | B2 | 3/2008 | Rose et al. |
| 9,044,453 | B2 | 6/2015 | Cady et al. |
| 10,543,170 | B2 | 1/2020 | Kanikanti et al. |
| 11,147,764 | B2 | 10/2021 | Kanikanti et al. |
| 2003/0064101 | A1 | 4/2003 | Mehta et al. |
| 2005/0032719 | A1 | 2/2005 | Cottrell et al. |
| 2006/0067954 | A1 | 3/2006 | Cottrell et al. |
| 2015/0342889 | A1 | 12/2015 | Kanikanti et al. |
| 2020/0113823 | A1 | 4/2020 | Kanikanti et al. |

FOREIGN PATENT DOCUMENTS

| EP | 1308163 A1 | 5/2003 |
| EP | 1197215 B1 | 3/2006 |
| EP | 2662075 A1 | 11/2013 |
| JP | H0374397 A | 3/1991 |
| JP | H07138150 A | 5/1995 |
| JP | 2008/508270 A | 3/2008 |
| JP | 2016/503767 A1 | 2/2016 |
| RU | 2214820 C2 | 10/2003 |
| WO | 2005013714 A1 | 2/2005 |
| WO | WO2005062782 A2 | 7/2005 |
| WO | 2005084688 A1 | 9/2005 |
| WO | 2006/022759 A1 | 3/2006 |
| WO | 2008/134819 A1 | 11/2008 |
| WO | 2008148027 A1 | 12/2008 |
| WO | 2014/095845 A1 | 6/2014 |
| WO | WO2014095845 A1 | 6/2014 |
| WO | WO2015071668 A1 | 5/2015 |
| WO | WO-2018065826 A1 * | 4/2018 ........... A61K 9/2086 |

OTHER PUBLICATIONS

Am Ende, M. et al. (2007) "Improving the Content Uniformity of a Low-Dose Tablet Formulation Through Roller Compaction Optimization," Pharmaceutical Development and Technology, 12:391-404.
International Search Report and Written Opinion, dated Feb. 9, 2018 for International Application No. PCT/EP2017/081049, filed Nov. 30, 2017, 12 pages.
Orr, N.A. et al. (1978) "Content uniformity of potent drugs in tablets," J. Pharm. Pharmac., 30:741-747.
Rohrs, B.R. et al. (May 2006) "Particle Size Limits to Meet USP Content Uniformity Criteria for Tablets and Capsules," J. Pharm. Sci., 95(5):1049-1059.

(Continued)

*Primary Examiner* — Snigdha Maewall
(74) *Attorney, Agent, or Firm* — McBee Moore & Vanik IP, LLC; Susan McBee

(57) ABSTRACT

The present invention refers to a pharmaceutical preparation (10) comprising a first pharmaceutical composition having a matrix material and pharmaceutically active ingredients distributed within the matrix material, wherein the first pharmaceutical composition comprises Praziquantel, Pyrantel and Febantel as pharmaceutical active ingredients, wherein the preparation (10) comprises a second pharmaceutical composition having a matrix material and at least one of avermectins and milbemycins such as Moxidectin as pharmaceutically active ingredient distributed within the matrix material, wherein the preparation (10) is provided in a multi-layer structure such, that the first composition is provided in a first layer (12) and the second composition is provided in a second layer (14), wherein the first layer (12) and the second layer (14) are separated by a barrier layer (16) being provided between the first layer (12) and the second layer (14).

17 Claims, 1 Drawing Sheet

(56) References Cited

OTHER PUBLICATIONS

Yalkowsky, S.H. et al. (1990) "Particle Size and Content Uniformity," Pharmaceutical Research, 7(9):962-966.
Zhang, Y. et al. (1997) "Effect of drug particle size on content uniformity of low-dose solid dosage forms," International Journal of Pharmaceutics, 154:179-183.
Jariwala et al., "A Review on Multiple Compressed Tablets", Journal of Pharmaceutical Bioscientific Research, 2016, pp. 371-379, vol. 6, No. 2.
Cobb et al., "Moxidectin: a review of chemistry, pharmacokinetics and use in horses", Parasites & Vectors, 2009, pp. 1-8, 2(Suppl 2):S5.
Kharkevich, Pharmacology, textbook, 2010, pp. 72-73. (machine translation).

* cited by examiner

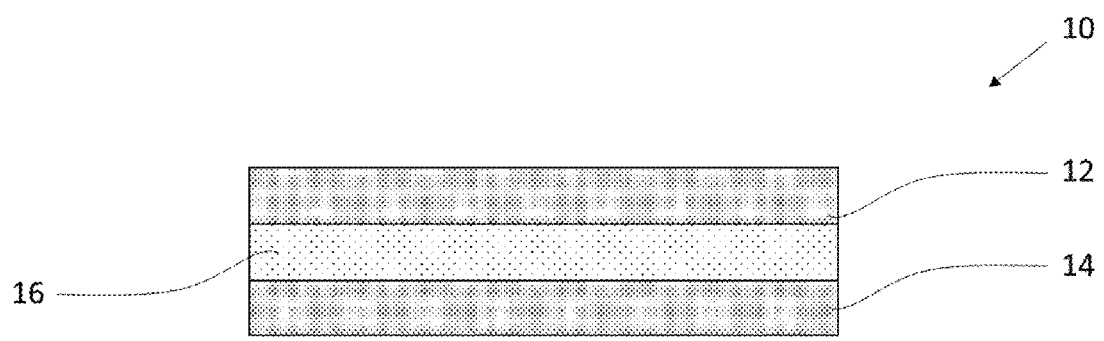

PHARMACEUTICAL PREPARATION AND METHOD FOR ITS MANUFACTURE

CROSS REFERENCE TO RELATED APPLICATIONS

This application is a National Phase application under 35 U.S.C. § 371 of International Application No. PCT/EP2017/081049, filed Nov. 30, 2017, which claims priority benefit of European Application No. 16203308.8, filed Dec. 9, 2016.

TECHNICAL FIELD

The present disclosure relates to a pharmaceutical preparation comprising a plurality of pharmaceutically active ingredients. The disclosure also relates to a method of manufacturing such a preparation.

BACKGROUND

Solid pharmaceutical preparations are often provided with a plurality of active ingredients. Especially such preparations require sufficient content uniformity in particular in case the active ingredients are present in a low dosage. With this regard, different documents are known dealing with content uniformity of drugs which may be a particular issue for low dosed drugs.

Am Ende M. T. et al., Pharm Devel Tech 12(4) (2007) pp. 391-404, describes studies which are directed to the question whether drug uniformity for a low-dosed granulated product may be affected by roller compaction and milling processing. Thus results were achieved for improving drug content uniformity.

Zhang Y. et al., Int J Pharma 154 (1997) pp. 179-183 describes studies demonstrating that the particle size has an effect on the content uniformity of a low dose drug-excipient blend and further shows calculations which may be used for simulating the respective results.

Orr N. A. et al., J Pharm Pharmac 30(1) (1978) pp. 741-747 deals with the distribution of low dosage drugs that occurs in batches of tablets and thus with the uniformity of drugs in tablets. In detail, examinations were made regarding the content uniformity of a solid dosage form containing a small amount of potent drug.

Rohrs R. B. et al., J Pharm Sci 95(5) (2006) pp. 1049-1059 deals with examining USP Content Uniformity by using defined physical and mathematical parameters for respective tests. It is described that satisfactory tablets of low doses cannot be manufactured from a drug that does not meet certain particle size distribution specifications.

Yalkowsky S. H. et al., Pharm Res 7(9) (1990) pp. 962-966 shows examinations referring to particle size and content uniformity of drugs. This document in detail describes results which shall be improved due to using the same descriptors for particle size and distribution.

Lactose—by DMV-Fonterra Excipients GmbH & Co. KG, 12 pages, describes that achieving good tablet content uniformity requires drug particles size to be controlled such that there are enough particles in a single dose to achieve adequate distribution. Further parameters which are described to be advantageously taken into consideration are the mixing strategy and the excipients used.

It is further known that different active ingredients may interact with each other thus, for example, negatively influencing the stability of respective compounds.

U.S. Pat. No. 6,489,303 B2 as well as EP 1 197 215 B1 for example describe anthelmintic compositions combining two or more active compounds. In more detail, these documents describe an anthelmintic composition combining an Antibiotic S541 compound preparable by fermentation of a *Streptomyces* microorganism, or a chemical derivative thereof, and another anthelmintically active compound, wherein the composition is stabilised by between about 0.15% and about 5.0% of an antioxidant by weight of the total anthelmintic composition. Such compositions may particularly form solutions.

U.S. Pat. No. 7,348,027 B2 further describes a method of preparing an oral self-take veterinary formulation. The veterinary formulation includes at least one active component that is undesirable to at least one of the senses of a target animal for the formulation. The method includes the steps of combining the active component and a masking component, which may be a mixture of ingredients that provide taste or scent masking properties, compressing this first mixture to form a crude tablet or slug, grinding the slug to form particles of greater density than the material prior to the first compression, and compressing the formulation a second time to form the final self-take tablet of acceptable hardness.

WO 2014/095845 A1 relates to tablets for animals with improved acceptance and good storage stability. Such a tablet comprises at least one active pharmaceutical ingredient, at least 28% by weight of meat flavouring and at least 2% by weight of a stabilizing agent.

It is the object of the present disclosure to provide a pharmaceutical preparation which has a uniform distribution even at low dosages and which may further show improved properties especially regarding the stability of more than one active ingredient provided therein in particular for low-dosed ingredients.

This object has been achieved with a pharmaceutical preparation according to claim 1 and a method according to claim 10. Preferred embodiments are given in the dependent claims and the further description. They may be combined freely and may form part of the present preparation unless the context clearly indicates otherwise.

DETAILED DESCRIPTION OF THE INVENTION

The present disclosure provides a pharmaceutical preparation comprising a first pharmaceutical composition having a matrix material and pharmaceutically active ingredients distributed within the matrix material, wherein the first pharmaceutical composition comprises Praziquantel, Pyrantel and Febantel as pharmaceutical active ingredients, wherein the preparation further comprises a second pharmaceutical composition having a matrix material and at least one of avermectins and milbemycins as pharmaceutically active ingredient distributed within the matrix material, wherein the preparation is provided in a multi-layer structure such, that the first composition is provided in a first layer and the second composition is provided in a second layer, wherein the first layer and the second layer are separated by a barrier layer being provided between the first layer and the second layer.

Such a preparation shows a very good behaviour with regard to stability of the provided pharmaceutically active ingredients and may further be produced easily. Pharmaceutical preparations according to the present disclosure may particularly be administered to carnivorous or omnivorous pets such as cats or dogs.

The described preparation especially addresses oral delivery systems containing low-dose potent drugs which are sensitive to oxygen, temperature and/or high humidity and which should be administered in combination one or more further pharmaceutically active ingredients.

The present disclosure further particularly describes a solid preparation which may be formed and thus be administered in the form of a tablet.

The term pharmaceutically active ingredient is thereby used throughout the following description corresponding to the known expressions "drug", "drug substance" or "API".

In some embodiments, a pharmaceutical preparation provided herein comprises a first pharmaceutical composition having a matrix material and Praziquantel, Pyrantel and Febantel as pharmaceutical active ingredients being distributed within the matrix material, and a second pharmaceutical composition having a matrix material and at least one of avermectins and milbemycins, such as Moxidectin, as pharmaceutically active ingredient distributed within the matrix material.

It is often the case that the different pharmaceutically active ingredients interact with each other or further components. Such an interaction may negatively influence specific ingredients and may thus lead to a reduced stability exemplarily leading to a reduced shelf-life. A combination of different pharmaceutically active ingredients are therefore often accompanied with additional substances being present in a comparably large amount in a combined pharmaceutical composition. Examples for such additional substances are comparably high doses of anti-oxidants which may prevent or reduce degradation of pharmaceutically active ingredients. However, such measures often leave room for improvements especially with regard to effectiveness and a long shelf life.

According to a preparation as described before, this problem however is not solved by using additional stabilisers and thus further additives being present in a common composition comprising a plurality of pharmaceutical active ingredients, but it is provided that the preparation is provided in a multi-layer structure such, that the first composition is provided in a first layer and the second composition is provided in a second layer, wherein the first layer and the second layer are separated by a barrier layer being provided between the first layer and the second layer.

In some embodiments, the preparation consists of said three layers. In some embodiments, the preparation comprises more than three layers.

Such an arrangement of the preparation is especially advantageous in that the provision of a barrier layer spatially separates the first pharmaceutical composition having a matrix material and Praziquantel, Pyrantel and Febantel as pharmaceutical active ingredients being distributed within the matrix material, and the second pharmaceutical composition comprising a matrix material and at least one of avermectins and milbemycins as pharmaceutically active ingredient distributed within the matrix material. Therefore, an interaction of different compounds being present in different layers, or compositions, respectively, may be securely avoided.

Such an arrangement may be particularly valuable in case, as stated before, at least one of avermectins and milbemycins, such as Moxidectin, as pharmaceutically active ingredient is separated from a composition having Praziquantel, Pyrantel and Febantel as pharmaceutical active ingredients.

Avermectins are a series of drugs used to treat parasitic worms. Milbemycins are a group of macrolides chemically related to the avermectins and are used in veterinary medicine as antiparasitic agents against worms, ticks and fleas. Under these drug classes, Moxidectin is a very effective member of these classes. In the following, even though the description is in detail disclosed with regard to Moxidectin, the person skilled in the art unambiguously knows that all features and effects which are described for Moxidectin, in the same or a comparable apply for the further examples of these substance classes.

Moxidectin as pharmaceutically active ingredient, for example, is a potent broad-spectrum endectocide of the macrocyclic lactone (macrolide) antimicrobial class and closely related to the milbemycins chemical group. It is an anthelmintic drug which kills parasitic worms (helminths), and is used for the prevention and control of heartworm and intestinal worms. It is produced by fermentation process using the fungal organism of the genus Streptomyces.

Moxidectin is thus a highly potent veterinary parasiticide and is active even at <25 µg/kg body weight and is thus particularly usable as a low-dosed drug. It may be characterized as white to pale yellow powder; M.W.: 639.84; m.p. 145-154° C.; practically insoluble in water and readily soluble in organic solvents. Moxidectin typically exists in amorphous form (Ph. Eur., 8.0/1656). However, certain crystalline forms are reported such as in U.S. Pat. No. 9,044,453 B2.

Moxidectin such as further examples of avermectins and milbemycins is sensitive to oxidation and moisture and/or high temperatures. Therefore to stabilize the drug substance during shelf-life is a challenge, which is solved according to the present preparation as well as method as described down below.

In some embodiments, Moxidectin is provided in the second composition in an amorphous form. In some embodiments, Moxidectin is present in the second composition as a solid dispersion, in particular with a polymer, such as the matrix material or an excipient. It has surprisingly been found that especially when Moxidectin is present in an amorphous form and further even more as a solid dispersion, it may be stabilized by a preparation as described before and by a method as described below in a very effective manner. The same is the truth for the further examples of avermectins and milbemycins.

Regarding the pharmaceutically active ingredients, especially when using at least one of avermectins and milbemycins, such as Moxidectin in the second pharmaceutically active composition, it may be preferred that the first pharmaceutically active composition comprises more than one pharmaceutical active ingredient in order to get a pharmaceutically active composition having a broad spectrum of usability.

With this regard, according to the present preparation, the first pharmaceutical composition comprises Praziquantel, Pyrantel and Febantel as pharmaceutical active ingredients. In an especially preferred manner, it may be provided that the first pharmaceutical composition is formed such, as it is known under the name Drontal Plus (DP, DP90) and which is in detail described in WO 2014/095845 A1.

Especially a combination of at least one of avermectins and milbemycins, such as Moxidectin, together with a preparation containing Praziquantel, Pyrantel and Febantel as pharmaceutical active ingredients provides a combination of four pharmaceutically active ingredients which in turn provides a very effective preparation usable as a so-called all-wormer for dogs, which is very attractive as pharmaceutically active preparation.

In detail, preferred actives in accordance with the first pharmaceutically active composition thus comprise or consist of Febantel (CAS No. 58306-30-2), Praziquantel (CAS No. 55268-74-1), and Pyrantel (CAS No. 22204-24-6). These endoparasitizides are normally used with dogs. Praziquantel kills mature and immature development stages of tapeworms in the intestine after a single treatment. Within a few seconds of a tapeworm coming into contact with Praziquantel its interaction with phospholipids and proteins causes damage to the tegument of the tapeworm. The subsequent inflow of calcium ions causes an immediate contraction of the entire strobila. Moreover, these changes lead to a reduction of glucose intake and an accelerated depletion of energy reserves of the tapeworm. Pyrantel, also known as Pyrantel Embonate, is an anthelmintic of the tetrahydropyrimidine group of compounds, and acts in a similar way to levamisol, by inducing a depolarising neuromuscular blockade. Pyrantel, being a cholinergic agonist, acts as an excitatory neurotransmitter at the nicotinergic receptor causing spastic paralysis of the parasite. The mode of action of Febantel is primarily based on interference with the carbohydrate metabolism of the parasitic worm. The resulting suppression of mitochondrial reactions (inhibition of fumarate reductase) and interference with glucose transport acts not only on all developmental stages of the helminths but also on the eggs containing the larvae. Benzimidazoles bind to the structural protein tubulin, thereby preventing its polymerization to microtubules that provide the transport system for the absorbing cells. The consequence of blocking this transport activity is incomplete absorption and digestion of nutrient particles and cellular autolysis through activation of lysosomal enzymes.

The combination of these three ingredients is marketed currently as DRONTAL PLUS, and the combination possesses an extremely wide spectrum of activity. It is used to treat infestation by dog roundworms and tapeworms including: *Toxocara canis, Toxascaris leonina, Uncinaria stenocephala, Ancylostoma caninum, Echinococcus granulosus, Echinococcus multilocularis, Dipylidium caninum, Taenia* spp., *Multiceps multiceps, Mesocestoides* spp., and *Trichuris vulpis* (whipworms).

However, especially in combination with the further pharmaceutical active ingredient Moxidectin, a very effective pharmaceutical preparation may be achieved. It has thereby been found that especially in case a single composition comprises Praziquantel, Pyrantel and Febantel next to Moxidectin, the stability of the latter may be reduced. Therefore, especially such an embodiment is advantageous with regard forming the preparation as a three-layer structure as described before. The same applies for the further examples of avermectins and milbemycins.

Due to the positive effects as described before, it was very promising to provide a pharmaceutical preparation having at least the four pharmaceutically active ingredients as described before. However, due to stability reasons especially of avermectins and milbemycins, such as Moxidectin, such a beneficial composition was hard to realize in the prior art but may be achieved very effectively and in a very stable manner according to the preparation as described before.

In some embodiments, the first and the second composition contain the respective active ingredient in a pharmaceutically effective amount, "pharmaceutically effective amount" meaning a non-toxic amount of active ingredient which can bring about the desired effect. The amount of active ingredient used depends on the active ingredient, the animal treated and on the nature, severity and stage of the disease.

Regarding the first pharmaceutical composition, it may be provided that all pharmaceutically active ingredients are present in the first composition in an amount of about from 5 to 50% by weight of active ingredient(s). The first composition can particularly contain from 10 to 50% by weight, for example from 15 to 40% by weight, or from 15 to 30% by weight of active ingredient(s).

The amount of active ingredient can also be specified as weight first pharmaceutical composition, for example at least 5 mg, at least 10 mg, at least 20 mg, at least 30 mg, at least 40 mg, at least 50 mg, or at least 100 mg of active ingredient(s). For example, it can contain from 5 to 2000 mg, from 10 to 1500 mg, from 10 to 1000 mg, from 10 to 500 mg, from 20 to 2000 mg, from 20 to 1500 mg, from 20 to 1000 mg, from 20 to 500 mg, from 50 to 2000 mg, from 50 to 1500 mg, from 50 to 1000 mg or from 50 to 500 mg of active ingredient(s).

Febantel is preferably used in the first pharmaceutical composition in concentrations of from 9 to 20% by weight, preferably from 11 to 17% by weight, particularly preferably from 12 to 16% by weight, referring to the first composition.

Praziquantel is preferably used in the first pharmaceutical composition in concentrations of from 1 to 10% by weight, preferably from 2 to 8% by weight, particularly preferably from 3 to 7% by weight, referring to the first composition.

Pyrantel, more particularly its embonate, is preferably used in the first pharmaceutical composition in concentrations of from 8 to 20% by weight, preferably from 9 to 17% by weight, particularly preferably from 11 to 15% by weight, referring to the first composition.

Further, Febantel may be present in the preparation, such as in a tablet, in an amount of $\geq 1$ wt. % to $\leq 25$ wt. %, particularly of $\geq 2.5$ wt. % to $\leq 20$ wt. %, for example of $\geq 3.8$ wt. % to $\leq 16$ wt. %, referring to the weight of the whole preparation.

Further, Praziquantel may be present in the preparation, such as in a tablet, in an amount of of $\geq 0.1$ wt. % to $\leq 20$ wt. %, particularly of $\geq 0.2$ wt. % to $\leq 13$ wt. %, for example of $\geq 0.4$ wt. % to $\leq 8$ wt. % referring to the weight of the whole preparation.

Further, Pyrantel may be present in the preparation, such as in a tablet, in an amount of $\geq 0.1$ wt. % to $\leq 25$ wt. %, particularly of $\geq 1.5$ wt. % to $\leq 20$ wt. %, for example of $\geq 2.5$ wt. % to $\leq 16$ wt. %, referring to the weight of the whole preparation.

Regarding the whole preparation, it may be provided that all pharmaceutically active ingredients are present in the first composition in an amount of about from 0.5 to 75% by weight of active ingredients referring to the whole preparation. The first composition tablets formed therewith can particularly contain from 3.5 to 60% by weight, for example from 6 to 50% by weight, such as from 6.5 to 40% by weight.

The first composition may for example contain the above-named pharmaceutically active ingredients, at least 28% by weight of meat flavouring and at least 2% by weight of a stabilizing agent, wherein the further components may be formed by one or more excipients and further additives, if required.

Further components of the first composition may comprise the matrix material. Such matrix material may be formed by an excipient as generally known per se and therefore in case an excipient is described throughout this description, the same may apply for a matrix material. In detail, excipients may be comprised such as polyvinylpyrrolidones, polyvinylpyrrolidone derivatives, polyethylene glycols, polyglycolized glycerides, lauroyl polyoxyl glycerides, stearoyl polyoxyl glycerides, hydroxyalkyl celluloses, hydroypropylmethylcelluose acetate succinate, polyvinyl caprolactam-polyethylene glycol-polyvinyl acetate-polyethylene glycol graft copolymers and/or copolymers of dimethylaminoethyl methacrylate, butyl methacrylate and methyl methacrylate, and furthermore povidone, copovidone, polyvinyl acetate-polyvinylcaprolactame-polyethyleneglycol graft copolymer (PVAc-PVCap-PEG, marketed as Soluplus®), Cellulose ethers, alkylmacroglycerides (Gelucires®), hydroxypropylmethylcellulose acetate succinate (HPMCAS), amino methacrylate copolymer (e.g. Eudragit E®) or the like.

Preferred are polyvinylpyrrolidones (povidones, PVP) and their derivatives. Various types of PVP are commercially available. PVP of relatively low molecular weight are normally employed as binders for tablets. It is possible by using PVP having different molecular weights to vary the kinetics of release within a defined range.

The polyvinylpyrrolidones or polyvinylpyrrolidone derivatives are normally linear and not crosslinked to ensure their water-solubility. The polyvinylpyrrolidones or polyvinylpyrrolidone derivatives normally have a K value of at least 10. The K value of the polyvinylpyrrolidones or polyvinylpyrrolidone derivatives is related to the viscosity and the molecular weight and can be determined by methods known per se. If in doubt, the data on the K value from the European Pharmacopeia (Ph. Eur.) are used. Preference is given to the use of polyvinylpyrrolidones and/or polyvinylpyrrolidone derivatives with a K value of from 10 to 90, particularly preferably 22 to 35.

A flavouring ingredient palatable to carnivores may further be added to the first composition. Such a flavouring may be a meat aroma. Suitable as meat aroma are dry liver powders from cattle, poultry, sheep or pigs, preferably from poultry and pigs, and other aroma preparations. In a preferred embodiment, suitable flavourings and aromatizers are mixtures of proteins, fats and carbohydrates which are specially processed; particular mention may be made of Artificial Beef Flavor® from Pharma Chemie (Syracuse, Nebr., USA). Artificial Beef Flavor® is a pig liver extract to which further proteins are added. In a further preferred embodiment, it is also possible to employ only liver powders.

In order to make the tablet attractive to carnivores such as dogs, a significant amount of flavour may be incorporated (e.g. so called pork liver granules to the extent of 10 to 55 weight %, preferably 20 to 50 weight % and more preferably 25 to 45 weight %, the weight percentage being based on the total weight of the composition). The flavour granules may be prepared by roller compacting a mixture of pork liver powder with suitable inert pharmaceutically known excipients such as maize starch and microcrystalline cellulose.

The first composition may thus comprise Praziquantel, Pyrantel and Febantel as pharmaceutically active ingredients, one or more excipients, flavours and further additives. In case Pyrantel is named, the latter may comprise the form of its salts, such as pyrantel embonate.

As avermectins and milbemycins, such as Moxidectin, may as well be sensitive against such flavours, to prevent the degradation of e.g. Moxidectin in presence of meat flavour, it is thus especially advantageous to provide three-layer tablet containing a barrier layer between e.g. Moxidectin and Drontal Plus layers in the case where the first composition and thus the Drontal Plus layer comprises a flavouring ingredient such as defined before.

Regarding the amount of the pharmaceutical active ingredient and thus of the at least one of avermectins and milbemycins, for example of Moxidectin in the second pharmaceutical composition it may be provided that such compound is generally present according to the desired need. In the following, even if the amount of Moxidectin is described, the latter is as well valid for the other examples of avermectins and milbemycins, in particular for all of avermectins and milbemycins present. In case the composition, e.g. a tablet comprising such a composition, is formed for 10 kg body weight of the animal, particularly dog, it may be provided that Moxidectin is present in the second composition of the preparation in an amount of ≤250 µg, such as in an amount of ≥0.005 wt. % to ≤0.5 wt. %, in particular in an amount of ≥0.02 wt. % to ≤0.3 wt. %, even more particularly in an amount of ≥0.035 wt. % to ≤0.15 with regard to the second composition.

Taking the whole preparation, it may be provided that the concentration of e.g. Moxidectin in the preparation, such as in a tablet which is ready for use, may lie in a range of ≥0.000050 wt. % to ≤0.5 wt. %, particularly of ≥0.00010 wt. % to ≤0.3 wt. %, for example of ≥0.00020 wt. % to ≤0.15 wt. %, referring to the preparation.

Like indicated above, Moxidectin or further avermectins and milbemycins is a very potent drug and may be present at comparably low dosages. The above dosages are already sufficient to provide an effective pharmaceutical preparation. The further components, next to the at least one of avermectins and milbemycins, such as Moxidectin, and the anti-oxidant, of the second pharmaceutical composition may comprise the matrix material. Such matrix material of the second pharmaceutical composition may be an excipient as described above with regard to the first composition.

Generally, it may be provided that Moxidectin is present as only drug in the second composition and thus as well as only drug from the group of avermectins and milbemycins. However, generally more than one drug may be provided, such as Moxidectin and one or more further of avermectins and milbemycins or one or more other examples of avermectins and milbemycins than Moxidectin.

In order to further stabilize avermectins and milbemycins, such as Moxidectin, it may be advantageous that the second composition and thus the composition comprising at least one of avermectins and milbemycins further comprises an anti-oxidant. According to this embodiment, the stability of the at least one of avermectins and milbemycins in the composition may be significantly improved. Suitable anti-oxidants may generally be chosen as known from the prior art. However, it has been found the sensitivity against oxidation of at least one of avermectins and milbemycins may be counteracted especially effectively in case the anti-oxidant is selected from the group consisting of butylated hydroxytoluene (BHT), propylgallate, and tocopherol. It may further be provided that the anti-oxidant is present in the second pharmaceutical composition in an amount of ≥0.005 wt. % to ≤1.5 wt. %, in particular in an amount of ≥0.05 wt. % to ≤1.0 wt. %., even more particularly in an amount of ≥0.062 wt. % to ≤0.7 wt. %. Generally, the anti-oxidant may be present in an amount of ≥0.5 times the concentration in wt. % to ≤4 times the concentration in wt. % of the at least one of avermectins and milbemycins, such as of Moxidectin.

It may be provided that the second composition comprises at least one of avermectins and milbemycins, for example Moxidectin, one or more anti-oxidants and one or more excipients. For example, the second composition may consist of only these components.

With regard to the barrier layer, it may be advantageous that this layer consists of one or more inert materials. With this regard, it may be provided that the barrier layer solely is formed of one or more materials, which show no interaction or reactions with the components being present in the first and second composition. Especially, the term inert material in the sense of the present disclosure shall mean that the one or more materials of the barrier layer do not negatively influence the stability of the pharmaceutically active ingredients of the first and the second pharmaceutically active composition.

For example, the one or more materials of the barrier layer may be selected from materials known as being usable as matrix materials like described in detail above. For example, the first composition may comprise a matrix material and the second composition may comprise a matrix material, wherein the matrix material of the first layer and of the second layer is the same, and wherein the barrier layer is formed from the matrix material used for the first composition and the second composition. As an alternative example, the first composition may comprise a matrix material and the second composition may comprise a matrix material, wherein the matrix material of the first layer and of the second layer is the different, and wherein the barrier layer is formed from the matrix material used for the first composition or the second composition or a further different material. As an alternative example, the first composition may comprise a matrix material and the second composition may comprise a matrix material, wherein the matrix material of the first layer and of the second layer is the same or different, and wherein the barrier layer is formed from a matrix material being different from the matrix material of the first and second layer.

In order to get a very effective separation effect of the barrier layer, it may be provided that the barrier layer has a thickness in the range of ≥0.1 mm to ≤5 mm. Such a thickness may provide a very effective barrier effect securely avoiding negative effects to the stability of pharmaceutically effective ingredients and further allow forming the preparation comparably thin and with a small amount of material providing advantages with respect to applicability and costs.

Oral dose forms for dogs, for example, containing low-dose potent drugs especially when being sensitive to oxygen, humidity or temperature are to be uniformly distributed in a matrix material to obtain good blend uniformity of granules. As an example of such low-dose drugs, especially Moxidectin as an example of avermectins and milbemycins is to be named, which may have a dose of less than 40 µg/kg body weight (bw). Like stated before, it is very advantageous to use such a pharmaceutically active ingredient in combination with the so-called Drontal Plus, or Moxid Plus, respectively, which is a combination of Praziquantel, Pyrantel embonate and Febantel as pharmaceutical active ingredients.

According to the prior art, it is extremely difficult to reach the goal, i.e. a mixture exhibiting good blend uniformity with the conventional granulation techniques used in pharmaceutical industry for such low-dose potent drugs. Such requirements, however, may be reached according to the present disclosure.

Additionally certain diluents like microcrystalline cellulose, lactose, mannitol, spray dried mannitol, spray dried sorbitol, dicalcium phosphate, or a commercially available excipients' mixture, such as the one being known under the names Prosolv® SMCC may be used in the range of 5 to 99.5 wt. % based on the total weight of the first and/or second composition and/or of the barrier layer.

To facilitate the dissolution of the tablet, super disintegrants like crospovidone, croscarmellose sodium, sodium starch glycolate, carmellose calcium, low substituted hydroxypropylcellulose (L-HPC), co-processed materials like Ludiflash (coprocessed mannitol, crospovidone, PVA and povidone), ParteckODT (spray-dried mannitol and croscarmellose sodium), Pearlitol Flash (directly compressible mannitol and starch), etc. or a combination thereof may be used in the range of 5 to 20 weight %, preferably 7.5 to 15 weight %, based on the total weight of the first and/or second composition and/or of the barrier layer.

To avoid segregation during the tableting process, the blend of materials must flow evenly into the dies of the tablet press. To facilitate this, certain glidants like colloidal silicon dioxide, talc may be added in the range 0.1 to 1.0 weight %, preferably in the range of 0.15 to 0.75 weight % and most preferably 0.2-0.5 weight %, based on the total weight of the first and/or second composition and/or of the barrier layer.

To avoid sticking of the materials to the punches and dies of the tablet press, small concentrations of a lubricant like magnesium stearate or sodium stearyl fumarate may be added in the range 0.1 to 1.0 weight %, preferably in the range of 0.15 to 0.75 weight % and most preferably 0.2 to 0.5 weight %, based on the total weight of the first and/or second composition and/or of the barrier layer.

It may further be advantageous that the matrix material of the first composition and/or of the second composition and/or the barrier layer further comprises a surfactant. A surfactant having a hydrophilic/lipophilic balance (HLB) value of ≥10 and preferably a non-ionic one (e.g. sodium lauryl sulfate, polyoxyl castor oils and/or EO/PO block copolymers) is particularly useful in increasing the availability of the pharmaceutically active ingredient (I) in aqueous media.

Preferably, the compositions or the barrier layer contain starch or a starch derivative as filler, which also acts to a certain extent as a disintegrant. Starch can, for example, be starch from wheat, rice, corn, tapioca, rye, oats or potatoes. Modified starches can be physically pretreated starches such as precooked starch or chemically altered starches such as hydroxyethyl starch, hydroxypropyl starch, methyl starch, carboxymethyl starch, starch acetate, hydroxypropyl starch acetate, hydroxyethyl starch acetate, starch phosphates, starch sulphates, or chemically or ionically cross-linked starches such as distarch phosphates, phosphates of hydroxypropylated starches, starch dicarboxylic diesters or salts of anionic starch derivatives. Preferably, starch, such as corn starch for example, is present as filler, specifically in amounts of typically from 5 to 30% by weight, preferably from 8 to 20% by weight, particularly preferably from 10 to 15% by weight, based on the total tablet weight.

The compositions or the barrier layer may further contain a further filler, such as microcrystalline cellulose, maltodextrin; a sugar such as sucrose, glucose or lactose; inorganic fillers, such as calcium carbonate, dicalcium phosphate or magnesium carbonate. Preference is given to using microcrystalline cellulose or more particularly lactose. Lactose is a commercially available pharmaceutical excipient which is available in various forms, for example spray-dried or as anhydrous lactose. In some embodiments, preference is given to using lactose monohydrate (e.g. milk sugar, fine from DMV International). In some embodiments, the preparation may contain from 5 to 20% by weight of lactose, preferably from 6 to 15% by weight, particularly preferably from 8 to 12% by weight, based on the total tablet weight.

The compositions or the barrier layer according to some embodiments preferably contain microcrystalline cellulose or a comparable excipient. Microcrystalline cellulose is a commercially available pharmaceutical excipient (e.g. Avicel® PH 101 from FMC). The preparation according to some embodiments contain from 2 to 10% by weight, preferably from 5 to 10% by weight, particularly preferably from 5.5 to 8% by weight, based on the total tablet weight. In an alternative embodiment, the tablets contain preferably from 3 to 8% by weight and particularly preferably from 4 to 6% by weight, based on the total tablet weight.

The compositions or the barrier layer may preferably contain silicon dioxide, more particularly colloidal anhydrous silicon dioxide, in amounts of from 0.01 to 0.3% by weight, more particularly from 0.05 to 0.2% by weight, based on the total tablet weight.

Furthermore, the compositions or the barrier layer can contain a binder, such as povidone for example. Povidone refers to hydrophilic polyvinylpyrrolidone polymers, those with a K-value of 30 or less preferably being used as binder. Povidone is used in concentrations of from 0.5 to 5% by weight, preferably from 1 to 3% by weight.

Furthermore, the compositions or the barrier layer can contain sodium lauryl sulphate or a comparable excipient. Sodium lauryl sulphate is used in concentrations of from 0.05 to 1% by weight, preferably from 0.1 to 0.3% by weight.

The present disclosure further relates to a method of manufacturing a pharmaceutical preparation like described above, wherein the method comprises the steps of:

A) Providing a first pharmaceutical composition having a matrix material and pharmaceutically active ingredients distributed within the matrix material, wherein the first pharmaceutical composition comprises Praziquantel, Pyrantel and Febantel as pharmaceutical active ingredients;
B) Providing a second pharmaceutical composition having a matrix material and at least one of avermectins and milbemycins, such as Moxidectin, as pharmaceutically active ingredient distributed within the matrix material;
C) Providing a barrier layer; and
D) Forming a multi-layer structure such, that the first composition is provided in a first layer and the second composition is provided in a second layer, wherein the first layer and the second layer are separated by the barrier layer being provided between the first layer and the second layer.

Such a method thus provides a pharmaceutically active preparation which shows a significant improved stability behavior of respective pharmaceutically active ingredients, in particular of at least one of avermectins and milbemycins, such as Moxidectin.

Like stated above with regard to the preparation, such a method provides an arrangement being especially advantageous in that the provision of a barrier layer spatially separates the first pharmaceutical composition having a matrix material and Praziquantel, Pyrantel and Febantel as pharmaceutical active ingredients being distributed within the matrix material, and the second pharmaceutical composition comprising a matrix material and at least one of avermectins and milbemycins, such as Moxidectin, as pharmaceutically active ingredient distributed within the matrix material. Therefore, an interaction of different compounds being present in different layers, or compositions, respectively, may be securely avoided.

Such an arrangement may be particularly valuable in case, as stated before, the at least one of avermectins and milbemycins as pharmaceutically active ingredient is separated from a composition having Praziquantel, Pyrantel and Febantel as pharmaceutical active ingredients.

According to the method as described before, according to process step A), a first pharmaceutical composition is provided and according to process step B), a second pharmaceutical composition is provided.

With this regard, the pharmaceutically active ingredients being present in the first or the second composition may generally be chosen according to the specific needs. However, like stated before, it may be especially advantageous in case the second composition comprises at least one of avermectins and milbemycins, especially Moxidectin, and that the first composition comprises Praziquantel, Pyrantel and Febantel as pharmaceutical active ingredients and thus the mixture called Drontal Plus.

With regard to the specific concentrations as well as to the additives, it is referred to the description of the preparation.

Like indicated above, it is extremely difficult to reach the goal, i.e. a mixture exhibiting good blend uniformity with the conventional granulation techniques used in pharmaceutical industry for such low-dose potent drugs, such as Moxidectin, for example. Such requirements, however, are fulfilled according to the present method.

It was surprisingly found that the method as described before provides significant advantages over the prior art. In particular, it could be found that the method as described before is superior in case at least one of avermectins and milbemycins, such as Moxidectin, is used as a pharmaceutical active ingredient. The latter may be the truth especially in case at least one of avermectins and milbemycins, such as Moxidectin, is used in an amorphous form in combination with DP90 like described in detail above with regard to the preparation.

In detail, the pharmaceutical composition produced as described has significant advantages with regard to stability for example over prior art solutions in which e.g. Moxidectin is solved in a solvent eventually with additives and add this solution to a blend of DP90 and form the latter mixture to a tablet.

If the quantity of the aqueous granulation fluid of a binder, like for example, HPMC 5 cP, is large enough, one could potentially homogeneously distribute Moxidectin such as in the form of a powder in the carrier excipient while granulating in a granulator. The water used must be eliminated by drying the granulate e.g. in a fluid bed drier for a relatively long time, during which e.g. Moxidectin is exposed to heat and oxygen. This is detrimental for drug stability.

Another alternative is to use non-inflammable and pharmaceutically acceptable solvents in which Moxidectin as an example of avermectins and milbemycins and an antioxidant like, for example BHT, are soluble, such as propylene glycol. To absorb the solvent, significantly higher amount of carrier material must be used leading to unacceptable increase in the volume and weight of the final dosage form. Consequently, the concentration of Moxidectin in the final blend decreases which in turn potentially causes content uniformity problems for the final dosage form.

Further, in case an ethanolic solution of Moxidectin as an example of avermectins and milbemycins and an antioxidant is added to the aqueous solution of HPMC and the slurry obtained is dried in a vacuum oven, wherein the dried mixture is milled and diluted with MCC or partially gelatinized starch (starch 1500), the blend shows inhomogeneous distribution of the active ingredient. Inspite of mixing with glidants like colloidal silicondioxide, the blend did not flow uniformly into the die of the tablet press.

When the slurry described above is used as granulating fluid and granulated with inter excipients like MCC in a granulator, the blend uniformity of the dried mixture is also unsatisfactory. When MCC is replaced by starch 1500, the mixture when dried could not be milled and processed further.

The above problems and drawbacks, however, are effectively overcome by using a method as described before and especially in case an embodiment as described below is used.

It may be especially advantageous in that step B) is provided by using at least one of avermectins and milbemycins, such as Moxidectin, in amorphous form and by forming a solid dispersion out of the amorphous drug and a polymeric material.

According to another aspect, the present disclosure further covers a pharmaceutical composition comprising a matrix material and at least one of avermectins and milbemycins, particularly Moxidectin, distributed within the matrix material, wherein the at least one of avermectins and milbemycins is provided in the composition as a solid dispersion.

Although the characteristics of the solid dispersions of avermectins and/or milbemycins are explained herein mainly by reference to the above mentioned pharmaceutical preparation, particularly with reference to the mentioned second pharmaceutical composition in the pharmaceutical preparation, and the method of manufacturing the preparation, these characteristics and the according benefits are also applicable to such solid dispersions according the other aspect of the present disclosure of the afore-mentioned paragraph.

The term "solid dispersion" can be defined as a dispersion of a drug in an amorphous polymer matrix where the drug is preferably in the molecularly dispersed state.

The two-component systems of solid dispersions can form multiple structures depending on their composition and sample processing history. When the drug loading is lower than the equilibrium solubility of drug in polymer, the drug is molecularly dispersed within the polymer and should form a thermodynamically stable, homogeneous solution. This is the most desirable structure of solid dispersion. However, for most drug-polymer pairs, this situation only appertains at very low drug loading and/or high temperature. As temperature is decreased, the mixture becomes a supersaturated solution and the drug tends to precipitate out. This can result in a dispersion of crystalline drug particles in a polymer matrix, in which the drug concentration corresponds to its equilibrium solubility at that temperature. Alternatively, as drug crystallization is a slow process with a higher energy barrier compared to amorphous phase separation, an intermediate meta-stable structure may form in which amorphous drug aggregates are dispersed in a polymer matrix containing drug at its amorphous solubility at that temperature.

Molecular dispersions, as solid dispersions, represent the last state on particle size reduction, and after carrier dissolution the drug is molecularly dispersed in the dissolution medium. Solid dispersions apply this principle to drug release by creating a mixture of a poorly water soluble drug and highly soluble carriers. A high surface area is formed, resulting in an increased dissolution rate and, consequently, improved bioavailability of pharmaceutically active ingredients which would otherwise only hardly be bioavailable, such as particularly Moxidectin or further examples of avermectins and milbemycins.

It was surprisingly found that the method as described before especially using a solid dispersion provides significant advantages over the prior art. Especially, a very good blend uniformity could be reached which may be preferable especially for low-dosed pharmaceutically active ingredients.

In case of avermectins and milbemycins such as particularly Moxidectin, especially in case the drug substance exists per se in amorphous form, an average skilled person in the field never comes to the idea of making a solid dispersion of e.g. Moxidectin. It is all the more unthinkable since amorphous forms are inherently i.e. thermodynamically unstable, sensitive to mechanical stress, moisture etc. and hence are not the choice of a formulation scientist. Latter in fact normally prefers to use thermodynamically stable crystals of a particular particle size distribution to develop a solid dosage form. If required, formulator would decrease the particle size of the crystalline drug substance (leading to higher surface area and faster dissolution in gastric mileu) to get the needed bioavailability.

The authors surprisingly found that the technology that is used to convert crystalline substances to their amorphous form is extremely suitable for stabilizing the amorphous Moxidectin i.e to retain the original amorphous nature of Moxidectin on storage during the shelf-life of the delivery system containing Moxidectin. Respective solid dispersions exhibit super saturation of Moxidectin since the latter exists in an amorphous form in solid dispersions and hence the probability of the drug getting absorbed in gastro-intestinal mileu due to high-trans-membrane flux without being recrystallized is relatively high. This is additionally the truth for further examples of avermectins and milbemycins.

This Moxidectin granulate or further examples of avermectins and milbemycins so prepared is mixed with other conventional excipients and is used as one of the three layers of the tablet, like shown in detail down below.

To summarize the above, it has surprisingly been found that using a method as described before, a very good blend uniformity especially of Moxidectin or further examples of avermectins and milbemycins could be reached, which can further be improved when using specific embodiments like described down below. Further, such a method is simple and economic. The demands according to which a granulate being capable of being dosed accurately into the die of the tablet machine, the granulate exemplarily containing Moxidectin as pharmaceutically active ingredient, are well realized by the method as described here.

Solid dispersions according to the present disclosure can exemplarily made by co-dissolving the drug and excipients, such as polymers, in one or more solvents which are miscible. The solvent or solvent mixture is later removed to form the solid dispersion. A further embodiment may comprise adding the drug to molten excipients and then cooling the mixture. This method is the basis of spray chilling (spray congealing), melt/emulsification/chill-hardening, hot-melt extrusion and injection moulding.

With regard to process step A), the first preparation may generally be formed as it is described in WO 2014/095845 A1. With this regard, it may be provided that the pharmaceutical ingredients and the matrix material as well as further additives may be mixed, granulated and for example milled. These steps may be realized with all components of the first composition. It may further be provided that additional components, such as meat flavour, are added after milling.

In detail, the first composition can be prepared according to a method in which
(a) the active ingredient(s), and any further excipients, is/are mixed, granulated, and the granules may be ground if necessary,
(b) the meat flavouring and any further excipients are added to the mixture from (a) and everything is processed, such as mixed, to form a homogeneous compressible mixture.

Further, the tablets according to some embodiments can be prepared according to a method in which
(a) the active ingredient(s), and any further excipients, is/are mixed, granulated, and the granules screened if necessary,
(b) the meat flavouring is homogenously mixed and dry granulated possibly with further excipients, and (c) any further excipients are added to the mixture from (a) and (b) and everything is processed, such as mixed, to form a homogeneous compressible mixture.

Preparation steps (a) can be carried out as wet granulation. Alternatively, preparation steps (a) can be carried out as dry granulation; the missing components are then processed in a separate wet granulation procedure. It is also possible for all components to be dry granulated with croscarmellose sodium in one step. Thereafter, mixing is carried out with, for example, magnesium stearate and colloidal silicon dioxide to obtain a compressible mixture.

Regarding the components of the first composition, it is referred to the preparation like described above.

With regard to step B), according to an embodiment, process step B) and thus particularly the formation of a solid dispersion comprising at least one of avermectins and milbemycins, such as Moxidectin, as pharmaceutically active ingredient may be realized by a method comprising the following steps:

B1) Providing a solution of at least one of avermectins and milbemycins, in particular of Moxidectin, and an excipient, such as a polymer, in a solvent;
B2) Applying the solution to a carrier; and
B3) Evaporating the solvent.

With regard to the solution performed according to process step B1), this solution may solely comprise, or consist of, respectively, at least one of avermectins and milbemycins, such as of Moxidectin, an excipient such as a polymer and a solvent. However, in order to improve the stability of the drug, it may be provided that the solution which is provided in step B1) further comprises an anti-oxidant. With regard to the anti-oxidant and the further components of the first composition it is referred to the above description of the preparation.

In detail, Moxidectin or a further example of avermectins and milbemycins along with a hydrophilic polymer as excipient, such as an excipient as described before, are dissolved in one or more miscible organic solvents to obtain a clear solution. Examples for solvents comprise ethanol, diethyl ether, dichloromethane, ethyl acetate, acetone, or mixtures of the before-named solvents. An antioxidant such as butylated hydroxytoluene (BHT), propylgallate, tocopherol, or the like may also be dissolved in the above solution. The concentration of Moxidectin or a further example of avermectins and milbemycins may lie in the range of $\geq 5$ wt.-% to $\leq 50$ wt.-%, preferably in the range of $\geq 10$ wt.-% to $\leq 40$ wt.-%, most preferably in the range of $\geq 10$ wt.-% to $\leq 40$ wt.-%. Further, the concentration of the excipient may lie in the range of $\geq 5$ wt.-% to $\leq 75$ wt.-%, preferably in the range of $\geq 15$ wt.-% to $\leq 65$ wt.-%, most preferably in the range of $\geq 25$ wt.-% to $\leq 60$ wt.-% and/or the concentration of the antioxidant may lie in the range of $\geq 5$ wt.-% to $\leq 40$ wt.-%, preferably in the range of $\geq 7.5$ wt.-% to $\leq 30$ wt.-%.

According to process step B2), the solution, such as the solution of Moxidectin, which was provided in step B1), is applied, such as sprayed, to a carrier, such as a polymer. With this regard, the carrier may be formed by lactose, microcrystalline cellulose, croscarmellose sodium or a further excipient as described before or mixtures of these components. This step may be realized by using an appropriate fluid bed granulator, for example.

Further, according to process step B3), the solvent of the solution such as comprising Moxidectin is evaporated. This may be realized by using an explosion-proof oven, such as a vacuum oven, under adequate conditions. In fact, the temperature of the oven may be adjusted in dependence of the solvents used, for example.

After evaporating the solvent, the first composition may be finished. With this regard, even though at least one of avermectins and milbemycins such as Moxidectin has a comparably low concentration, it was found that it is provided in a very good content uniformity allowing a very well applicability.

According to a further embodiment, process step B) and thus the formation of a solid dispersion comprising at least one of avermectins and milbemycins such as Moxidectin as pharmaceutically active ingredient may be realized by a method comprising the following steps:

B1) Providing a solution of at least one of avermectins and milbemycins, such as Moxidectin, and an excipient, such as a polymer, in a solvent;
B4) Evaporating the solvent; and
B5) Milling the product of step B4).

With regard to the process step B1), it may be referred to the step B1) as described before.

According to this embodiment, however, according to process step B4), the solvent is evaporated directly after which according to process step B5), the product of process step B4) is milled.

In particular, again, it may be provided that in process step B1), a solution may be provided of the pharmaceutical active ingredient in particular together with additives. As an example, it may be provided that the present method uses an ethanolic solution of Moxidectin, BHT and povidone. The so provided solution may be dried by evaporating the solvent (step B4) and the dried such as in a vacuum oven and the product may be milled afterwards (step B5). When the resulting material is milled, it may be mixed with further inert excipients, such as MCC, in order to get the second pharmaceutical composition.

As a non-limiting example, Moxidectin or a further example of avermectins and milbemycins along with an anti-oxidant, such as BHT, and a carrier (such as Povidone, HPMC) are dissolved in a suitable solvent, such as ethanol. The resulting solution of drug, polymer and the antioxidant in organic solvent(s) is poured on to trays to a thickness of 0.3 to 5 cm thickness and dried in ex-rated vacuume oven at temperatures <40° C. until the residual solvent limits are well within the approved limits of Ph. Eur. The dried cake is milled/screened (eg. <0.5 mm screen) and used for the next step, i.e., manufacturing of the tablets. To facilitate the drying process, even the partially dried cake may be screened through a coarse screen (eg. 3 mm) and dried further until the above mentioned target for the residual solvent(s) is reached. The dried material is milled and mixed with suitable inert excipients to obtain a blend showing good blend uniformity and that can be used to compress solid dosage forms, such as tablets, exhibiting acceptable content uniformity.

According to a still further embodiment, process step B) and especially providing at least one of avermectins and milbemycins such as Moxidectrin comprises the formation of a solid dispersion comprising at least one of avermectins and milbemycins such as Moxidectin as pharmaceutically active ingredient, which may be realized by a method comprising the following steps:

B6) Providing an excipient, such as a polymer;
B7) Providing at least one of avermectins and milbemycins such as Moxidectin;
B8) extruding the excipient with the at least one of avermectins and milbemycins such as Moxidectin; and
B9) Milling the product of step B8).

Especially, in case the excipient has a relatively low melting point such as e.g. Gelucires®, the drug substance, e.g Moxidectin may be incorporated into the polymer which is plasticized during extrusion. The drug and polymer with the antioxidant(s) is extruded for example in a twin screw extruder fitted with a nozzle of e.g. 0.6 mm diameter at a temperature which may lie at 25° C. The friction generated within the extruder due to the kneading blocks present in the screws, is sufficient to soften the polymer. The drug substance and the antioxidant are homogeneously distributed in the softened polymer. The extruded string is processed further by gentle milling process to obtain the solid dispersion of the desired particle size (eg. <0.5 mm).

Therefore, this embodiment may be especially advantageous in case the melting point or softening point of the excipient is low enough that an introduction of the drug into the excipient may be realized by the energy which is provided by the screw or screws of the extruder. With regard to the milling step, it is referred to the above description.

Regarding the first composition, the second composition and the barrier layer, the present method further comprises according to process step D) Forming a multi-layer structure such, that the first composition is provided in a first layer and the second composition is provided in a second layer, wherein the first layer and the second layer are separated by a barrier layer being provided between the first layer and the second layer. With regard to the specific structure, it is referred to the description of the preparation as can be seen before. Further, with regard to preparing the tablet, generally methods may be used as it is generally known in the art.

In the animal health sector, i.e. in the field of veterinary medicine, the present solid pharmaceutical preparations can be used to control animal parasites, in particular ectoparasites. Ectoparasites are typically and preferably arthropods, especially insects such as flies (biting and licking), parasitic fly larvae, lice, hair lice, bird lice, fleas and the like; or acarids such as ticks, for example hard ticks or soft ticks, or mites such as scab mites, harvest mites, bird mites and the like. These parasites include the following ectoparasites (in particular insects, acarids):

From the order of the Anoplurida, for example, *Haematopinus* spp., *Linognathus* spp., *Pediculus* spp., *Phthirus* spp. and *Solenopotes* spp.; specific examples are: *Linognathus setosus, Linognathus vituli, Linognathus ovillus, Linognathus oviformis, Linognathus pedalis, Linognathus stenopsis, Haematopinus asini macrocephalus, Haematopinus eurysternus, Haematopinus suis, Pediculus humanus capitis, Pediculus humanus corporis, Phylloera vastatrix, Phthirus pubis, Solenopotes capillatus;*

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.; specific examples are: *Bovicola bovis, Bovicola ovis, Bovicola limbata, Damalina bovis, Trichodectes canis, Felicola subrostratus, Bovicola caprae, Lepikentron ovis, Werneckiella equi;*

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomya* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; specific examples are: *Aedes aegypti, Aedes albopictus, Aedes taeniorhynchus, Anopheles gambiae, Anopheles maculipennis, Calliphora erythrocephala, Chrysozona pluvialis, Culex quinquefasciatus, Culex pipiens, Culex sarsalis, Fannia canicularis, Sarcophaga carnaria, Stomoxys calcitrans, Tipula paludosa, Lucilia cuprina, Lucilia sericata, Simulium reptans, Phlebotomus papatasi, Phlebotomus longipalpis, Odagmia ornata, Wilhelmia equina, Boophthora erythrocephala, Tabanus bromius, Tabanus spodopterus, Tabanus atratus, Tabanus sudeticus, Hybomitra ciurea, Chrysops caecutiens, Chrysops relictus, Haematopota pluvialis, Haematopota italica, Musca autumnalis, Musca domestica, Haematobia irritans irritans, Haematobia irritans exigua, Haematobia stimulans, Hydrotaea irritans, Hydrotaea albipuncta, Chrysomya chloropyga, Chrysomya bezziana, Oestrus ovis, Hypoderma bovis, Hypoderma lineatum, Przhevalskiana silenus, Dermatobia hominis, Melophagus ovinus, Lipoptena capreoli, Lipoptena cervi, Hippobosca variegata, Hippobosca equina, Gasterophilus intestinalis, Gasterophilus haemorroidalis, Gasterophilus inermis, Gasterophilus nasalis, Gasterophilus nigricornis, Gasterophilus pecorum, Braula coeca;*

From the order of the Siphonapterida, for example *Pulex* spp., *Ctenocephalides* spp., *Tunga* spp., *Xenopsylla* spp., *Ceratophyllus* spp.; specific examples are: *Ctenocephalides canis, Ctenocephalides felis, Pulex irritans, Tunga penetrans, Xenopsylla cheopis;*

From the order of the Heteropterida, for example, *Cimex* spp., *Triatoma* spp., *Rhodnius* spp. and *Panstrongylus* spp.;

From the order of the Blattarida, for example *Blatta orientalis, Periplaneta americana, Blattela germanica* and *Supella* spp. (e.g. *Suppella longipalpa*);

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Rhipicephalus (Boophilus)* spp., *Dermacentor* spp., *Haemophysalis* spp., *Hyalomma* spp., *Dermanyssus* spp., *Rhipicephalus* spp. (the original genus of multihost ticks), *Ornithonyssus* spp., *Pneumonyssus* spp., *Raillietia* spp., *Pneumonyssus* spp., *Sternostoma* spp., *Varroa* spp., *Acarapis* spp.; specific examples are: *Argas persicus, Argas reflexus, Ornithodorus moubata, Otobius megnini, Rhipicephalus (Boophilus) microplus, Rhipicephalus (Boophilus) decoloratus, Rhipicephalus (Boophilus) annulatus, Rhipicephalus (Boophilus) calceratus, Hyalomma anatolicum, Hyalomma aegypticum, Hyalomma marginatum, Hyalomma transiens, Rhipicephalus evertsi, Ixodes ricinus, Ixodes hexagonus, Ixodes canisuga, Ixodes pilosus, Ixodes rubicundus, Ixodes scapularis, Ixodes holocyclus, Haemaphysalis concinna, Haemaphysalis punctata, Haemaphysalis cinnabarina, Haemaphysalis otophila, Haemaphysalis leachi, Haemaphysalis longicorni, Dermacentor marginatus, Dermacentor reticulatus, Dermacentor pictus, Dermacentor albipictus, Dermacentor andersoni, Dermacentor variabilis, Hyalomma mauritanicum, Rhipicephalus sanguineus, Rhipicephalus bursa, Rhipicephalus appendiculatus, Rhipicephalus capensis, Rhipicephalus turanicus, Rhipicephalus zambeziensis, Amblyomma americanum, Amblyomma variegatum, Amblyomma maculatum, Amblyomma hebraeum, Amblyomma cajennense, Dermanyssus gallinae, Ornithonyssus bursa, Ornithonyssus sylviarum, Varroa jacobsoni;*

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.; specific examples are: *Cheyletiella yasguri*, *Cheyletiella blakei*, *Demodex canis*, *Demodex bovis*, *Demodex ovis*, *Demodex caprae*, *Demodex equi*, *Demodex caballi*, *Demodex suis*, *Neotrombicula autumnalis*, *Neotrombicula desaleri*, *Neoschongastia xerothermobia*, *Trombicula akamushi*, *Otodectes cynotis*, *Notoedres cati*, *Sarcoptis canis*, *Sarcoptes bovis*, *Sarcoptes ovis*, *Sarcoptes rupicaprae* (=*S. caprae*), *Sarcoptes equi*, *Sarcoptes suis*, *Psoroptes ovis*, *Psoroptes cuniculi*, *Psoroptes equi*, *Chorioptes bovis*, *Psoergates ovis*, *Pneumonyssoidic mange*, *Pneumonyssoides caninum*, *Acarapis woodi*.

The preparations according to some embodiments are also suitable for controlling arthropods which attack animals. The animals include agricultural livestock, for example cattle, sheep, goats, horses, pigs, donkeys, camels, buffalo, rabbits, chickens, turkeys, ducks, geese. The animals also include domestic animals—also referred to as companion animals—for example dogs, cats, caged birds, aquarium fish, and what are known as test animals, for example hamsters, guinea pigs, rats and mice.

The control of these ectoparasites should reduce cases of death and improve the performance (for meat, milk, wool, hides, eggs, honey etc.) and the health of the host animal, and so the use of the preparations according to some embodiments enables more economically viable and easier animal husbandry.

For example, it is desirable to prevent or to interrupt the uptake of blood from the host by the parasites (if relevant). Control of the parasites can also contribute to preventing the transmission of infectious substances.

The term "control" as used herein with regard to the field of animal health means that the active compounds act by reducing the occurrence of the parasite in question in an animal infested with such parasites to a harmless level. More specifically, "control" as used herein means that the active compound kills the parasite in question, retards its growth or inhibits its proliferation.

EXAMPLES

The following examples are simply intended to further illustrate and explain embodiments of the present disclosure. The examples, therefore, should not be regarded as limiting the scope of the disclosure or manner it may be practiced. For examples, the percent of flavour granules in a tablet may be varied to suite the acceptance of the tablets by the dogs.

Especially, the following examples are shown with Moxidectin as a non-limiting example of avermectins and milbemycins. However, the same effects appear when using the further examples of avermectins and milbemycins in particular under the same or comparable conditions.

Amounts given in the examples below are parts by weight.

The preparation contains three distinct layers namely: Moxidectin layer (second layer), placebo layer called as intermediate or barrier layer and Drontal Plus layer (first layer comprising Praziquantel, Febantel and Pyrantel-Embonat).

I. Preparation of the Second Layer Comprising Moxidectin

The second layer is formed by forming a solution of Moxidectin and subsequently forming a solid dispersion thereof either by tray drying of in a fluid bed granulator. Afterwards, the Solid Dispersion is mixed with a matrix material.

I. (i) Preparation of a Solution and Forming a Solid Dispersion Thereof

The following solutions were used for forming a solid dispersion (the amount of solvent may be chosen such that all components are in solution):

| No. 1 | |
|---|---|
| Moxidectin | 1 part |
| BHT | 1.5 parts |
| Povidone K17 | 2 parts |
| Ethanol is used as solvent. | |

| No. 2 | |
|---|---|
| Moxidectin | 1 part |
| BHT | 1.5 parts |
| Povidone K17 | 3 parts |
| Ethanol is used as solvent. | |

| No. 3 | |
|---|---|
| Moxidectin | 1 part |
| BHT | 2 parts |
| Povidone K17 | 3 parts |
| Ethanol is used as solvent. | |

| No. 4 | |
|---|---|
| Moxidectin | 1 part |
| BHT | 3 parts |
| Povidone K17 | 3 parts |
| Ethanol is used as solvent. | |

| No. 5 | |
|---|---|
| Moxidectin | 1 part |
| BHT | 2 parts |
| Propylgallate | 1 part |
| Povidone K17 | 3 parts |
| Ethanol is used as solvent. | |

| No. 6 | |
|---|---|
| Moxidectin | 1 part |
| BHT | 3 part |
| Povidone K25 | 4 parts |
| Ethanol is used as solvent. | |

| No. 7 | |
|---|---|
| Moxidectin | 1 part |
| BHT | 3 parts |
| Propylgallate | 1 part |
| Povidone K25 | 3 parts |
| Ethanol is used as solvent. | |

| No. 8 | |
|---|---|
| Moxidectin | 1 part |
| BHT | 3 parts |
| Copovidone | 3 parts |
| Ethanol is used as solvent. | |

| No. 9 | |
|---|---|
| Moxidectin | 1 part |
| BHT | 3 parts |
| Soluplus ® | 3 parts |
| Ethanol is used as solvent | |

| No. 10 | |
|---|---|
| Moxidectin | 1 part |
| BHT | 3 parts |
| HPMC 5 cP | 3 parts |
| Ethanol & methylene chloride are used as solvents. | |

| No. 11 | |
|---|---|
| Moxidectin | 1 part |
| BHT | 3 parts |
| HPC -L | 3 parts |
| Ethanol is used as solvent. | |

-continued

| No. 12 | |
|---|---|
| Moxidectin | 1 part |
| BHT | 3 parts |
| HPMCAS | 3 parts |
| Ethanol & acetone are used as solvents. | |

| No. 13 | |
|---|---|
| Moxidectin | 1 part |
| BHT | 3 parts |
| Gelucire ® 50/13 | 3 parts |

| No. 14 | |
|---|---|
| Moxidectin | 1 part |
| BHT | 3 parts |
| Gelucire ® 46/14 | 3 parts |

The Moxidectin-polymer complex in the form of a solid dispersion is made together with the antioxidant(s) using the techniques described above. In detail, the solution formed as described above is either transferred to trays and dried in explosion-proof vac oven at <40° C. (tray drying process) or sprayed onto inert polymer carriers (such as lactose, microcrystalline cellulose, croscarmellose sodium or mixtures of inert excipients etc.) in an appropriate fluid bed granulator as mentioned above. The solid material obtained at the end is sieved (<0.5 mm) and assayed for the content of the drug substance.

I. (ii) Processing of the Solid Dispersion According to the Tray Dried Moxidectin-Polymer Complex into Final Blend which Forms the Second Composition is Ready for Compression for Tablet Formation Aliquot of the dried powder equivalent to 100 μg or 250 μg of moxdectin based on assay from any of the above examples 2, 3 and 4 is mixed with the excipient Prosolv® SM CC excipient and magnesium stearate as lubricant, the latter in a concentration ranging from 0.2-1.25 wt. %, and the resulting blend is used for making the Moxidectin layer of the final product. The ratio between moxidectin-polymer complex to Prosolv® SM CC is 1:400, preferably 1:200 or most preferably 1:144 with regard to weight.

Aliquot of the dried powder equivalent to 375 μg or 750 μg of moxdectin based on assay from any of the above examples 8, 9, 10 and 11 is mixed with the excipient Prosolv® SM CC excipient and magnesium stearate as lubricant the latter in a concentration ranging from 0.2-1.25%, and the resulting blend is used for making the Moxidectin layer of the final product. The ratio between moxidectin-polymer complex to Prosolv® SM CC is 1:400, preferably 1:200 or most preferably 1:144 with regard to weight.

I. (iii) Processing of the Moxidectin-Polymer Complex (Solid Dispersion) Prepared by a Fluid Bed Granulation Process into Final Blend which is Ready for Compression for Tablet Formation The organic solution mentioned in any of the examples 1-12 is sprayed on carrier material lactose monohydrate (ratio between Moxidectin to lactose monohydrate is 1:200) and dried until the residual solvent levels comply the requirements of Ph. Eur. An aliquot of this dried material equivalent to 100 or 250 or 375 or 750 μg of Moxidectin is mixed with a glidant (eg. colloidal silicon dioxide or talc) and finally with the lubricant (eg. magnesium stearate or sodium fumaryl stearate) to obtain the ready-to-compress mixture of the Moxidectin layer.

According to a further example, the carrier material is croscarmellose sodium instead of the lactose monohydrate.

I. (iv) Processing of the Moxidectin-Polymer Complex (Solid Dispersion) Prepared by an Extrusion Process into Final Blend which is Ready for Compression for Tablet Formation The composition according to examples 13 and 14 is extruded like stated above. It is extruded for example in a twin screw extruder fitted with a nozzle of e.g. 0.6 mm diameter at a temperature which may lie at 25° C. The friction generated within the extruder due to the kneading blocks present in the screws, is sufficient to soften the polymer. The drug substance and the antioxidant are homogeneously distributed in the softened polymer. The extruded string is processed further by gentle milling process to obtain the solid dispersion of the desired particle size (eg. <0.5 mm).

According to a further example, the carrier material is microcrystalline cellulose, instead of the lactose monohydrate.

According to a further example, the carrier material is a mixture of lactose monohydrate and microcrystalline cellulose.

The ratio between the Moxidectin to the carrier could vary from 1:50 to 1:400 or 1:800.

The concentration of the glidant in the Moxidectin layer ranges from 0.2-1.5%. Similarly, the concentration of the lubricant ranges from 0.2-1.25%.

II. Preparation of the Barrier Layer

A mixture of lactose monohydrate and microcrystalline cellulose (30:70) is mixed and wet granulated with an aqueous solution of povidone K17 (4%) in a high shear mixer. The wet blend is dried and passed through a screen (<0.5 mm) to obtain the dry granulate. This is mixed with the glidant, such as magnesium stearate, and lubricant, such as magnesium stearate, as described in moxidection layer.

Aliquot amount of the placebo granulate is used to make the intermediate layer i.e. the layer between the Moxidectin and Drontal plus layers. The thickness of the placebo layer is <5 mm in the final tablet.

III. Composition of the First Layer (Drontal Plus Layer)

The composition as well as the manufacturing process may be performed like described in WO2014/095845 A1.

Thus, firstly, a preblend may be formed in that Praziquantel, Febantel and Pyrantel-Embonat as well as cornstarch and lactose-monohydrate are mixed in a mixing granulator. The mixture is granulated with an aqueous mixture of povidone and sodium lauryl sulfate. Subsequently, the product is dried and screened.

Secondly, in order to form a postblend, meat flavour, corn starch and microcrystalline cellulose are mixed in a dry form, compacted and screened. In order to realize a mixture having a good fluidity, the meat flavour may have a moisture content according to Karl-Fischer-Titration of ≥5.5 wt. %.

In order to receive the final blend and thus the ready to press mixture, the quantity of the finalblend should be meant for a dog weighing 4 or 10 or 15 or 30 kg dogs. Moxidectin dose is 25 μg/kg dog weight. The respective amount of preblend and postblend is mixed with croscarmellose-sodium, magnesium stearate and waterfree silicon dioxide. This mixture can then be pressed in the form of tablets.

IV. Preparing a Tablet which is Ready for Use

In the following, examples are shown for producing a three-layer tablets meant for a dog weighing 10 kg.

IV. (i) Moxidectin Examples

Different examples are provided showing compositions of the second layer comprising 250 μg Moxidectin.

Moxidectin Example 1

| | |
|---|---|
| Solid dispersion as per example 2 | 1.375 mg |
| Prosolv ® SMCC | 198 mg |
| Magnesium stearate | 0.6 mg |
| Total weight | 199.975 mg |

Moxidectin Example 2

| | |
|---|---|
| Solid dispersion as per example 2 | 1.375 mg |
| Prosolv ® SMCC | 550 mg |
| Magnesium stearate | 1.2 mg |
| Total weight | 552.575 mg |

Moxidectin Example 3

| | |
|---|---|
| Solid dispersion as per example 3 | 1.5 mg |
| Prosolv ® SMCC | 216 mg |
| Magnesium stearate | 0.6 mg |
| Total weight | 218.1 mg |

Moxidectin Example 4

| | |
|---|---|
| Solid dispersion as per example 3 | 1.5 mg |
| Prosolv ® SMCC | 600 mg |
| Magnesium stearate | 1.2 mg |
| Total weight | 602.7 mg |

Moxidectin Example 5

| | |
|---|---|
| Solid dispersion as per example 6 | 2.0 mg |
| Prosolv ® SMCC | 288 mg |
| Magnesium stearate | 0.6 mg |
| Total weight | 290.6 mg |

Moxidectin Example 6

| | |
|---|---|
| Solid dispersion as per example 10 | 1.75 mg |
| Prosolv ® SMCC | 252 mg |
| Magnesium stearate | 0.6 mg |
| Total weight | 254.35 mg |

Moxidectin Example 7

| | |
|---|---|
| Solid dispersion as per example 10 | 1.75 mg |
| Prosolv ® SMCC | 700 mg |
| Magnesium stearate | 1.2 mg |
| Total weight | 702.95 mg |

Moxidectin Example 8

| | |
|---|---|
| Solid dispersion as per example 11 | 1.75 mg |
| Prosolv ® SMCC | 700 mg |
| Magnesium stearate | 1-2 mg |
| Total weight | 702.95 mg |

Moxidectin Example 9

| | |
|---|---|
| Solid dispersion as per example 12 | 1.75 mg |
| Prosolv ® SMCC | 252 mg |
| Magnesium stearate | 0.6 mg |
| Total weight | 254.35 mg |

IV. (ii) Composition of the Intermediate or Barrier or Placebo Layer

| | |
|---|---|
| Microcrystalline cellulose | 360.6 mg |
| Dicalcium phosphate anhydrous | 270.6 mg |
| Povidone K-25 | 33.6 mg |
| Colloidal silicon dioxide | 3.4 mg |
| Magnesium stearate | 1.8 mg |
| Total weight | 670.0 mg |

IV. (iii) Examples of the First Layer (Drontal Plus Layer)

In the following, an example of the first layer comprising Drontal Plus is shown.

Drontal Plus Example 1

| | |
|---|---|
| Febantel | 150.0 mg |
| Praziquantel | 50.0 mg |

-continued

|  |  |
|---|---|
| Pyrantel embonate | 144.0 mg |
| Lactose monohydrate | 100.0 mg |
| Corn starch | 143.0 mg |
| Povidone 25 | 18.00 mg |
| Sodium lauryl sulphate | 2.0 mg |
| Spray-dried liver powder | 355.4 mg |
| Microcrystalline cellulose | 49.0 mg |
| Croscarmellose sodium | 40.0 mg |
| Magnesium stearate | 3.0 mg |
| Anhydrous colloidal silicon dioxide | 1.0 mg |
| Total weight | 1055.4 mg |

To illustrate the present disclosure (without limiting to), three-layer tablets could be made for a dog weighing 10 kg by taking the composition of the Drontal Plus layer, moxidectin layer and the intermediate barrier layer using an appropriate commercially available tablet press. If a tablet for a smaller dog is to be prepared, then the above quantities are proportionately adjusted to suite the dog's weight.

If the 3-layer tablet is meant for a dog weighing 35 kg, the weight of the moxidectin and placebo layers is increased proportionately. The composition of the Drontal plus layer is given below:

Drontal Plus Example 2

|  |  |
|---|---|
| Febantel | 525.0 mg |
| Praziquantel | 175.0 mg |
| Pyrantel embonate | 504.0 mg |
| Lactose monohydrate | 350.0 mg |
| Corn starch | 500.5 mg |
| Povidone 25 | 63.0 mg |
| Sodium lauryl sulphate | 7.0 mg |
| Spray-dried liver powder | 1243.9 mg |
| Microcrystalline cellulose | 171.5 mg |
| Croscarmellose sodium | 280.0 mg |
| Magnesium stearate | 10.5 mg |
| Anhydrous colloidal silicon dioxide | 3.5 mg |
| Tablet weight | 3833.9 mg |

V. Stability of Moxidectin Three-Layer Tablets

As described before, chemical stability of moxidectin may be considered in some embodiments. 3-layer tablets manufactured according to some embodiments showed high stability and low degradation products like shown below.

Three Moxidectin solid dispersions (SD) differing in their antioxidant (BHT)-content were prepared as per the composition given below and according to the tray drying procedure described earlier. Later the respective solid dispersion is mixed with excipients, namely Prosolv® SMCC 50 and magnesium stearate in the ratios mentioned below and obtained a granulate-blend that is ready to be used for the moxidectin layer of the three-layer drug product.

Moxidectin solid dispersions "a, b and c":

Solid dispersion (a): Moxidectin (0.25 parts), Povidone K 17 (0.75 parts), BHT (0.125 parts) and Ethanol (10.3 parts).

Solid dispersion (b): Moxidectin (0.25 parts), Povidone K 17 (0.75 parts), BHT (0.25 parts) and Ethanol (10.3 parts).

Solid dispersion (c): Moxidectin (0.25 parts), Povidone K 17 (0.75 parts), BHT (0.5 parts) and Ethanol (10.3 parts).

Solid dispersions "a", "b" and "c" obtained above are mixed with Prosolv® SMCC 50 and magnesium stearate in the ratios mentioned below and obtained a granulate-blend that is the ready-to-use moxidectin layer of the three-layer drug product.

Moxidectin layer of SD "a": SD "a" (1.13 mg), Prosolv® SMCC 50 (198.27 mg), Magnesium stearate (0.60 mg).

Moxidectin layer of SD "b": SD "b" (1.25 mg), Prosolv® SMCC 50 (198.10 mg), Magnesium stearate (0.60 mg).

Moxidectin layer of SD "c": SD "c" (1.50 mg), Prosolv® SMCC 50 (197.85 mg), Magnesium stearate (0.60 mg).

Intermediate or barrier or placebo layer is same as that described above. The Drontal Plus layer of example 1 was used for one of the three layers. Three-layer tablets having different moxidectin SD layers were prepared. Moxidectin content in the tablet is 250 µg (meant for a dog weighing 10 kg). The tablets are placed in aluminum bags, sealed and stored at 30° C./75% RH. After 3 months, the moxidectin as well as the content of the related products (degradants) were assayed.

In order to show the degradation, the structures of Moxidectin (structure 1) and of the degradants are shown below (structure 2 corresponds to Degradant called 23-Z-Moxidectin and structure 3 corresponds to Degradant called 23-keto F-alpha). In the tables, eventually missing percent which are not defined by Moxidectin or the described degradants may be formed by further, non-specified degradants.

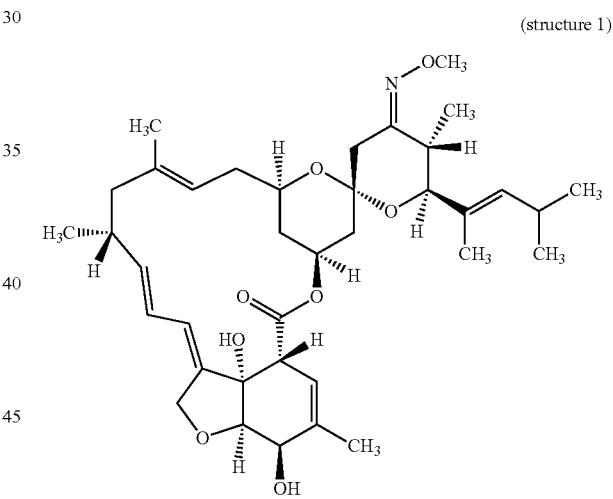

(structure 1)

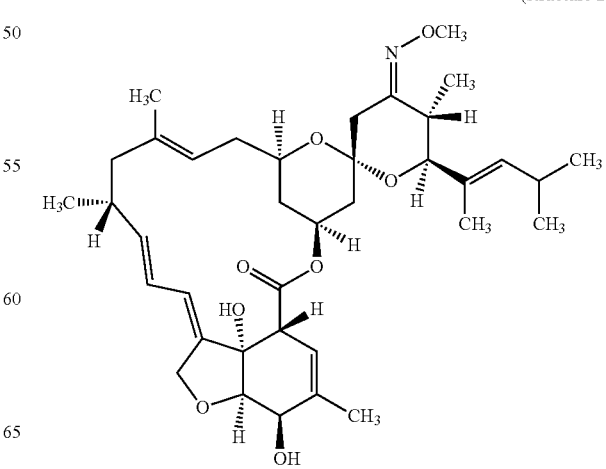

(structure 2)

-continued (structure 3)

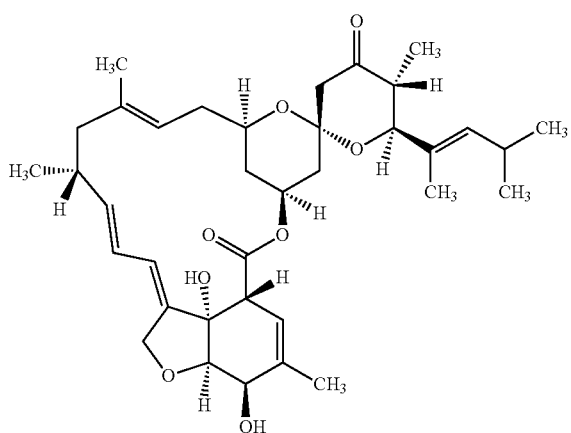

The data of the stability test (30° C./75% RH) are given below:

|  | three-layer tablets containing | | |
|---|---|---|---|
| Compound assayed | Moxidectin layer of SD "a" | Moxidectin layer of SD "b" | Moxidectin layer of SD "c" |
| Moxidectin | ≥[[99.4]]99.4% | ≥[[99.4]]99.4% | ≥[[99.4]]99.4% |
| Degradant, "23-keto F-alpha" | <0.3% | <0.3% | <0.3% |
| Degradant, "23-Z-Moxidectin" | <0.3% | <0.3% | <0.3% |

Comparative Example 1

Three different three-layer tablets containing identical amounts of all ingredients in each layer as above were prepared. The composition of all three layers is same as above except that the ready-to-use moxidectin layer does not contain the SD of moxidectin. The ingredients namely: moxidectin, Povidone K 17, BHT, Prosolv® SMCC 50 and magnesium stearate are mixed in dry form homogeneously and used as the moxidectin layer. The placebo and Drontal Plus layers are identical to those of the above formulations.

Moxidectin content in the tablet is also 250 μg (meant for a dog weighing 10 kg). The tablets are placed in aluminum bags, sealed and stored at 30° C./75% RH. After 3 months, the moxidectin as well as the content of the related products (degradants) were assayed. The data are given below:

|  | 3-layer tablets (moxidectin layer prepared by dry mixing) containing | | |
|---|---|---|---|
| Compound assayed | Moxidectin layer with composition identical to that of SD "a" | Moxidectin layer with composition identical to that of SD "b" | Moxidectin layer with composition identical to that of SD "c" |
| Moxidectin | 81% | 82% | 80% |
| Degradant, "23-keto F-alpha" | 14.4% | 13.7% | 15.8% |
| Degradant, "23-Z-Moxidectin" | 3.5% | 3.4% | 3.7% |

Comparative Example 2

Moxidation gets readily oxidized and hence anti-oxidant is needed as is the case with all the examples mentioned earlier. In this example, moxidectin layer is prepared by dry mixing as in comparative example 1. The exact composition of moxidectin layer is given below:

| Moxidectin | 0.25 mg |
|---|---|
| BHT | 1.5 mg |
| Prosolv® SMCC 50 | 197.6 mg |
| Magnesium stearate | 0.6 mg |

The placebo/barrier or intermediate layer as well as the Drontal Plus layer are identical to those mentioned earlier.

Three layer tablets are prepared, placed in aluminum bags, sealed and stored at 30° C./75% RH. After 3 months, the moxidectin as well as the content of the related products (degradants) were assayed. The data are given below:

| Compound assayed | % found |
|---|---|
| Moxidectin | 80 |
| Degradant, "23-keto F-alpha" | 1.5 |
| Degradant, "23-Z-Moxidectin" | 3.2 |

Although the content of anti-oxidant in comparative example 2 is 6 times the amount of the drug substance, the latter got degraded significantly.

This clearly shows the high inventiveness of some embodiments i.e. amorphous moxidectin has to be stabilized by making a complex with a polymer like povidone in presence of an antioxidant.

Therefore, according to the some embodiments it may be provided that the second composition comprises, referring to the second composition, an amount of ≤20 wt. %.

The invention claimed is:

1. A pharmaceutical preparation comprising:
   a first pharmaceutical composition having a matrix material and pharmaceutically active ingredients distributed within the matrix material; and
   a second pharmaceutical composition having a matrix material and at least one of avermectins and milbemycins as pharmaceutically active ingredient distributed within the matrix material,
   wherein the first pharmaceutical composition comprises Praziquantel, Pyrantel and Febantel as pharmaceutical active ingredients,
   wherein the preparation is provided in a multi-layer structure such that the first composition is provided in a first layer and the second composition is provided in a second layer, and the first layer and the second layer are separated by a barrier layer provided between the first layer and the second layer,
   wherein the matrix material of the first composition, of the second composition and of the barrier layer is different, or wherein the matrix material of the barrier layer is different from the matrix material of the first composition or of the second composition, and
   wherein the barrier layer has a thickness in the range ≥0.1 to ≤5 mm wherein the at least one of avermectins and milbemycins is present in the second composition in an amount of >0.005 wt. % to <0.5 wt. % and wherein the first pharmaceutical composition comprises pharmaceutical active ingredients in an amount of >5 wt. % to <50 wt. %.

2. The preparation of claim 1, wherein the at least one of avermectins and milbemycins is provided in the second composition as a solid dispersion.

3. The preparation of claim 1, wherein the at least one of avermectins and milbemycins is provided in the second composition in an amorphous form.

4. The preparation of claim 1, wherein the first pharmaceutical composition further comprises a flavouring ingredient.

5. The preparation of claim 1, wherein the second pharmaceutical composition further comprises an anti-oxidant.

6. The preparation of claim 1, wherein the barrier layer comprises one or more inert materials selected from the group consisting of polyvinylpyrrolidones, polyvinylpyrrolidone derivatives, polyethylene glycols, polyglycolized glycerides, lauroyl polyoxyl glycerides, stearoyl polyoxyl glycerides, hydroxyalkyl celluloses, hydroypropylmethylcelluose acetate succinate, polyvinyl caprolactam-polyethylene glycol-polyvinyl acetate-polyethylene glycol graft copolymers, copolymers of dimethylaminoethyl methacrylate, butyl methacrylate and methyl methacrylate, povidone, copovidone, polyvinyl acetate-polyvinylcaprolactame-polyethyleneglycol graft copolymer, cellulose ethers, alkylmacroglycerides, hydroxypropylmethylcellulose acetate succinate, and amino methacrylate copolymer.

7. A method of manufacturing a pharmaceutical preparation comprising:
  A) Providing a first pharmaceutical composition having a matrix material and pharmaceutically active ingredients distributed within the matrix material, wherein the first pharmaceutical composition comprises Praziquantel, Pyrantel and Febantel as pharmaceutical active ingredients;
  B) Providing a second pharmaceutical composition having a matrix material and at least one of avermectins and milbemycins as pharmaceutically active ingredient distributed within the matrix material;
  C) Providing a barrier layer; and
  D) Forming a multi-layer structure such that the first composition is provided in a first layer and the second composition is provided in a second layer, wherein the first layer and the second layer are separated by the barrier layer provided between the first layer and the second layer,
  wherein the matrix material of the first composition, of the second composition and of the barrier layer is different, or wherein the matrix material of the barrier layer is different from the matrix material of the first composition or of the second composition, and wherein the barrier layer has a thickness in the range ≥0.1 to ≤5 mm wherein the at least one of avermectins and milbemycins is present in the second composition in an amount of >0.005 wt. % to <0.5 wt. % and wherein the first pharmaceutical composition comprises pharmaceutical active ingredients in an amount of >5 wt. % to <50 wt. %.

8. The method of claim 7, wherein in step B), the at least one of avermectins and milbemycins is provided together with a polymer, an excipient, in the form of a solid dispersion, wherein the at least one of avermectins and milbemycins is provided in an amorphous form.

9. The method of claim 7, wherein step B) comprises the steps of:
  B1) Providing a solution of at least one of avermectins and milbemycins, and an excipient in a solvent;
  B2) Applying the solution to a carrier; and
  B3) Evaporating the solvent.

10. The method of claim 7, wherein step B) comprises:
  B1) Providing a solution of at least one of avermectins and milbemycins, and an excipient in a solvent;
  B4) Evaporating the solvent; and
  B5) Milling the product of step B4).

11. The method of claim 7, wherein step B) comprises:
  B6) Providing an excipient;
  B7) Providing at least one of avermectins and milbemycins;
  B8) extruding the excipient with the at least one of avermectins and milbemycins; and
  B9) Milling the product of step B8).

12. The method of claim 9, wherein the solution which is provided in step B1) further comprises an anti-oxidant.

13. The preparation of claim 1, wherein the at least one of avermectins and milbemycins is present in the second composition in an amount of ≥0.02 wt. % to ≤0.3 wt. %.

14. The preparation of claim 1, wherein the at least one of avermectins and milbemycins is present in the second composition in an amount of ≥0.035 wt. % to ≤0.15 wt. %.

15. The preparation of claim 1, wherein the first pharmaceutical composition comprises pharmaceutical active ingredients in an amount of ≥10 wt. % to ≤50 wt. %.

16. The preparation of claim 1, wherein the first pharmaceutical composition comprises pharmaceutical active ingredients in an amount of ≥15 wt. % to ≤40 wt. %.

17. The preparation of claim 1, wherein the first pharmaceutical composition comprises pharmaceutical active ingredients in an amount of ≥15 wt. % to ≤30 wt. %.

* * * * *